(12) United States Patent
Won et al.

(10) Patent No.: US 9,517,446 B2
(45) Date of Patent: *Dec. 13, 2016

(54) SUPER ABSORBENT POLYMER AND A PREPARATION METHOD THEREOF

(71) Applicant: LG CHEM, LTD., Seoul (KR)

(72) Inventors: Tae-Young Won, Daejeon (KR);
Chang-Sun Han, Daejeon (KR);
Gi-Cheul Kim, Daejeon (KR);
Yong-Hun Lee, Daejeon (KR);
Sang-Gi Lee, Daejeon (KR); Kyu-Pal Kim, Daejeon (KR); Sung-Soo Park, Daejeon (KR); Gyu Leem, Daejeon (KR)

(73) Assignee: LG Chem, Ltd. (KR)

( * ) Notice: Subject to any disclaimer, the term of this patent is extended or adjusted under 35 U.S.C. 154(b) by 0 days.

This patent is subject to a terminal disclaimer.

(21) Appl. No.: 14/394,685

(22) PCT Filed: Apr. 23, 2013

(86) PCT No.: PCT/KR2013/003465
§ 371 (c)(1),
(2) Date: Oct. 15, 2014

(87) PCT Pub. No.: WO2013/162255
PCT Pub. Date: Oct. 31, 2013

(65) Prior Publication Data
US 2015/0087742 A1   Mar. 26, 2015

(30) Foreign Application Priority Data

Apr. 25, 2012 (KR) .................. 10-2012-0043435
Apr. 23, 2013 (KR) .................. 10-2013-0044663

(51) Int. Cl.
| | | |
|---|---|---|
| *C08F 2/10* | (2006.01) |
| *B01J 20/30* | (2006.01) |
| *B01J 20/26* | (2006.01) |
| *C08F 220/06* | (2006.01) |
| *C08J 3/075* | (2006.01) |
| *C08J 3/12* | (2006.01) |
| *C08J 3/24* | (2006.01) |

(52) U.S. Cl.
CPC .......... *B01J 20/3085* (2013.01); *B01J 20/267* (2013.01); *C08F 220/06* (2013.01); *C08J 3/075* (2013.01); *C08J 3/12* (2013.01); *C08J 3/24* (2013.01); *C08J 3/245* (2013.01); *B01J 2220/68* (2013.01); *C08J 2300/14* (2013.01); *C08J 2333/02* (2013.01)

(58) Field of Classification Search
CPC . C08F 220/06; C08F 2222/1013; C08F 6/008; C08F 222/1006; C08F 120/06; C08F 20/06; C08F 265/06; A61L 15/60; A61L 15/24; A61L 15/26; A61L 15/22; A61L 15/225; A61L 15/00; A61L 26/0061; B01J 20/267; B01J 2220/68; B01J 20/265; B29B 2009/161
USPC ......... 522/181, 180, 329.7, 375, 330.3, 384, 55,522/402–402.24, 403, 404, 407, 321.1, 474.4,522/331, 389.9, 212, 213–213.36, 483, 256; 264/534, 5, 41, 4
See application file for complete search history.

(56) References Cited

U.S. PATENT DOCUMENTS

| | | |
|---|---|---|
| 5,314,420 A | 5/1994 | Smith et al. |
| 6,576,713 B2 * | 6/2003 | Ishizaki et al. ............ 525/329.7 |
| 2004/0048955 A1 | 3/2004 | Wada et al. |
| 2007/0161759 A1 * | 7/2007 | Riegel et al. ................. 525/375 |
| 2009/0215617 A1 | 8/2009 | Kimura et al. |
| 2010/0308263 A1 | 12/2010 | Torii et al. |
| 2011/0245436 A1 | 10/2011 | Gartner et al. |
| 2011/0257341 A1 | 10/2011 | Riegel et al. |
| 2012/0298915 A1 | 11/2012 | Okuda et al. |

FOREIGN PATENT DOCUMENTS

| | | |
|---|---|---|
| CN | 1578820 A | 2/2005 |
| CN | 1917954 A | 2/2007 |
| CN | 102174207 A | 9/2011 |
| EP | 1130045 A2 | 9/2001 |
| EP | 0872491 B1 | 5/2006 |
| JP | 56-161408 | 12/1981 |
| JP | 57-158209 | 9/1982 |
| JP | 57-198714 | 12/1982 |
| JP | H0233426 A | 2/1990 |
| JP | H07185331 A | 7/1995 |
| JP | 07-224204 | 8/1995 |
| JP | 10-060014 | 3/1998 |
| JP | H1160975 A | 3/1999 |
| JP | 2002-212204 | 7/2002 |

(Continued)

OTHER PUBLICATIONS

Buchholz et al., "Modem Superabsorbent Polymer Technology", copyright 1998.

(Continued)

*Primary Examiner* — James J Seidleck
*Assistant Examiner* — S. Camilla Pourbohloul
(74) *Attorney, Agent, or Firm* — Lerner, David, Littenberg, Krumholz & Mentlik, LLP

(57) ABSTRACT

The present invention relates to a super absorbent polymer (SAP) and a preparation method thereof. More specifically, the present invention provides a SAP satisfying the overall properties required to a SAP and especially the superior initial absorbency and absorbing rate under load at the same time, and a preparation method thereof, by treating the surface of the SAP with a surface treatment solution including water and a diol-based or glycol-based surface crosslinking agent.

6 Claims, No Drawings

(56) References Cited

FOREIGN PATENT DOCUMENTS

| | | |
|---|---|---|
| JP | 2002201290 A | 7/2002 |
| JP | 2003-062460 | 3/2003 |
| JP | 2003192732 A | 7/2003 |
| JP | 2004261797 A | 9/2004 |
| JP | 2004-300425 | 10/2004 |
| JP | 2005111474 A | 4/2005 |
| JP | 2006116535 A | 5/2006 |
| JP | 2007523254 A | 8/2007 |
| JP | 2009510177 A | 3/2009 |
| KR | 20010086145 A | 9/2001 |
| KR | 10-0298108 | 10/2001 |
| KR | 10-2004-0094776 | 11/2004 |
| KR | 20060009316 A | 1/2006 |
| KR | 10-2007-0094741 | 9/2007 |
| KR | 10-2009-0010219 | 1/2009 |
| KR | 10-2010-0014556 | 2/2010 |
| KR | 10-2011-0009580 | 1/2011 |
| KR | 10-2011-0049072 | 5/2011 |
| KR | 10-2011-0087293 | 8/2011 |
| KR | 10-2011-0111938 | 10/2011 |
| KR | 10-2011-0134333 | 12/2011 |
| KR | 10-2011-0136597 | 12/2011 |
| WO | 2004069915 A2 | 8/2004 |
| WO | 2006033477 A1 | 3/2006 |
| WO | 2007037522 A1 | 4/2007 |
| WO | 2011026876 A1 | 3/2011 |
| WO | 2011099586 A1 | 8/2011 |
| WO | 2011113728 A1 | 9/2011 |
| WO | 2011117187 A1 | 9/2011 |

OTHER PUBLICATIONS

International Search Report from PCT/KR2013/003465, dated Sep. 25, 2013.
Wolfrom, Rebecca Lea, "The Language of Particle Size." Particle Technology Labs, as Published in GXP, Spring 2011 (vol. 15, No. 2).
Search Report from European Application No. 13781735.9, dated Mar. 1, 2016.
Buchholz, et al., "Modern Superabsorbent Polymer Technology." John Wiley & Sons, Inc., 1998, pp. 69-103.

* cited by examiner

SUPER ABSORBENT POLYMER AND A PREPARATION METHOD THEREOF

TECHNICAL FIELD

The present invention relates to a super absorbent polymer that is superior in the initial absorbency and does not discharge moisture by pressure even after time has passed, and a preparation method thereof.

BACKGROUND OF THE INVENTION

Super absorbent polymer (SAP) is a synthetic polymer material having a function of absorbing water about 5 hundred times to about 1 thousand times of the weight of itself, and it has been differently named as super absorbency material (SAM), absorbent gel material (AGM), and so on by developing enterprises. The SAP disclosed above was started to be commercialized for sanitary items and is now being widely used to a water combination soil for horticulture, a water-stop material for civil engineering and construction, a nursery sheet, a freshness preservative in a food distribution field, a poultice material, and the like in addition to the sanitary fittings like a paper diaper for a child.

An inverse suspension polymerization method or an aqueous polymerization method is known as a method of preparing super absorbent polymer. For example, the inverse suspension polymerization is disclosed in Japanese Patent Publication Nos. Sho56-161408, Sho57-158209, Sho57-198714, and so on. As the aqueous polymerization method, a thermal polymerization method that polymerizes a polymer gel while fracturing and cooling the same in a kneader equipped with a spindle, and a photo-polymerization method that exposes a high-concentrated aqueous solution on a belt to UV rays and the like so as to carry out the polymerization and the dry at the same time are known.

Furthermore, the surface treatment of the resin powder obtained through the processes of polymerization, pulverization, drying, and final pulverization is being attempted for obtaining the hydrogel polymer having more excellent properties, or various modifications in the process are being attempted for improving the efficiency of polymerization, pulverization, and drying.

Meanwhile, the particle size, the absorbency, and the water holding property have been considered as important factors for evaluating the properties of the SAP, and many efforts have been made to improve the same. And, the concept of absorbing rate was introduced and the speed of absorption has been evaluated as the absorbing rate measured by using Vortex.

However, prior methods mentioned just the characteristics of each property, and did not mention the synergy effect when said properties are complexly combined. Furthermore, existing methods have mainly mentioned only the absorbing rate under non pressured condition of the SAP. Furthermore, they have not provided the SAP having rapid absorbing rate and good feelings of wearing at the same time until now.

DETAILS OF THE INVENTION

Objects of the Invention

It is an aspect of the present invention to provide a super absorbent polymer (SAP) having excellent property and absorbency that is especially superior in the initial absorbency and hardly discharge moisture by pressure even after long time has passed, and a preparation method thereof, through the surface treatment of the SAP.

It is another aspect of the present invention to provide a SAP having rapid absorbing rate and excellent wearing comfort at the same time, and a preparation method thereof.

Means for Achieving the Objects

The present invention provides a super absorbent polymer (SAP), having the SPAN value of 1.2 or less, represented by the following Mathematical Formula 1, and satisfying the absorbing rate under load represented by the following Mathematical Formula 2:

$$\text{SPAN} = [D(90\%) - D(10\%)]/D(50\%) \leq 1.2 \quad \text{[Mathematical Formula 1]}$$

in Mathematical Formula 1,
D(90%) is the diameter of the particle when the accumulated weight from the smallest particle becomes 90%,
D(10%) is the diameter of the particle when the accumulated weight from the smallest particle becomes 10%, and
D(50%) is the diameter of the particle when the accumulated weight from the smallest particle becomes 50%, $$1.0 > \text{ARUL} = \text{AUP}(10\ \text{min})/\text{AUP}(60\ \text{min}) > 0 \quad \text{[Mathematical Formula 2]}$$

in Mathematical Formula 2,
ARUL is the absorbing rate under load, AUP (10 min) is the absorbency under pressure after 10 mins represented by the following Mathematical Formula 3, and AUP (60 min) absorbency under pressure after 60 mins represented by the following Mathematical Formula 3, $$\text{AUP}(g/g) = [Wb(g) - Wa(g)]/\text{weight of absorbent polymer}(g) \quad \text{[Mathematical Formula 3]}$$

in Mathematical Formula 3,
Wa (g) is the sum of the weight of the absorbent polymer and the weight of the device capable of providing load to the absorbent polymer, and
Wb (g) is the sum of the weight of the absorbent polymer in which moisture is absorbed under load (0.7 psi) for a given time of 10 mins or 60 mins and the weight of the device capable of providing load to the absorbent polymer.

The super absorbent polymer may include a crosslinked polymer obtained by crosslinking the surface of a powdery base polymer prepared from at least partially neutralized water-soluble ethylenic unsaturated monomer including an acid group with a $C_2$-$C_8$ diol or glycol compound.

The present invention also provides a method of preparing the super absorbent polymer, including the steps of:
preparing a monomer composition including a water-soluble ethylenic unsaturated monomer and a polymerization initiator;
preparing a hydrogel polymer by polymerizing said monomer composition in a polymerization reactor;
drying and pulverizing said hydrogel polymer;
classifying said pulverized hydrogel polymer; and
treating the surface of said hydrogel polymer by spraying a surface treatment solution including water and a surface crosslinking agent on each of the classified hydrogel polymer particles.

At this time, the surface crosslinking agent may be a $C_2$-$C_8$ diol or glycol compound.

And, the surface treatment solution may further include one or more organic solvents selected from the group consisting of ethanol, methanol, isopropylalcohol, ethyleneglycol, propyleneglycol, polyethyleneglycol, and polypropyleneglycol.

The surface treatment solution may include 0.1 to 10 weight % of the surface crosslinking agent.

The surface crosslinking agent can be used through a pipe form or a nozzle but it is preferable that the solution is sprayed on the surface of the hydrogel polymer through the nozzle.

Furthermore, the step of treating the surface may include the steps of feeding the classified hydrogel polymer to a surface crosslinking reactor, and carrying out a surface crosslinking reaction of the hydrogel polymer at 120 to 250° C. for 10 to 120 mins.

And, the step of drying and pulverizing the hydrogel polymer may be carried out so that the particle size of the dried hydrogel polymer becomes 150 to 850 μm.

Furthermore, the classifying step may include the steps of:

classifying the pulverized hydrogel polymer into 2 grades of the particle size below 150 μm and the particle size of 150 μm to 850 μm;

classifying the pulverized hydrogel polymer into 3 grades of the particle size below 150 μm, the particle size of 150 μm or more and below 300 μm, and the particle size of 300 μm to 850 μm; or classifying the pulverized hydrogel polymer into 4 grades of the particle size below 150 μm, the particle size of 150 μm or more and below 300 μm, the particle size of 300 μm or more and below 600 μm, and the particle size of 600 μm to 850 μm.

The present method may further include the step of pulverizing and classifying the hydrogel polymer into the particles having the particle size of 150 to 850 μm after the step of treating the surface of the hydrogel polymer.

The method may further include the step of pulverizing the hydrogel polymer to have the particle size of 1 mm to 15 mm after the polymerization and before the step of drying the hydrogel polymer.

Effects of the Invention

According to the present invention, the SAP is superior in all properties such as the particle size, the initial absorbency, and the water holding property, and shows excellent absorbing rate under load (ARUL) satisfying a particular condition. Therefore, the SAP of the present invention can be used for preparing comfortable and wearable sanitary fittings because the content of rewetting, the content of moisture that comes out, is low even after a certain time passed.

DETAILED DESCRIPTION OF THE EMBODIMENT

Hereinafter, the preparation method of the SAP according to specific embodiment of the invention is explained in more detail.

The present invention is characterized in controlling the particle diameter through a proper classification during the pulverizing process, and especially in treating the surface of the particles by using a glycol-based solvent and a diol-based or glycol-based surface crosslinking agent with a specific amount and condition, and provides the method of preparing the SAP having very excellent absorbency even under a long time pressured state.

Therefore, the SAP according to the present invention is superior in the particle size and the properties, and especially, can show excellent absorbing rate under load (ARUL) satisfying a particular condition and can provide an excellent wearing sensation because the content of rewetting, the content of moisture that comes out, is low even after a certain time passed. Therefore, the SAP satisfying the properties of the specific parameter of the present invention can be widely used to a water combination soil for horticulture, a water-stop material for civil engineering and construction, a nursery sheet, a freshness preservative in a food distribution field, a poultice material, and the like in addition to various sanitary fittings.

The present invention provides a preparation method of the SAP having the SPAN value of 1.2 or less, represented by the following Mathematical Formula 1, and satisfying the absorbing rate under load represented by the following Mathematical Formula 2, according to one embodiment of the present invention:

$$\text{SPAN} = [D(90\%) - D(10\%)]/D(50\%) \leq 1.2 \quad \text{[Mathematical Formula 1]}$$

in Mathematical Formula 1,

D(90%) is the diameter of the particle when the accumulated weight from the smallest particle becomes 90 weight %, D(10%) is the diameter of the particle when the accumulated weight from the smallest particle becomes 10 weight %, and D(50%) is the diameter of the particle when the accumulated weight from the smallest particle becomes 50 weight %, $$1.0 > \text{ARUL} = \text{AUP}(10\ \text{min})/\text{AUP}(60\ \text{min}) > 0.70 \quad \text{[Mathematical Formula 2]}$$

in Mathematical Formula 2,

ARUL is the absorbing rate under load, AUP (10 min) is the absorbency under pressure after 10 mins represented by the following Mathematical Formula 3, and AUP (60 min) absorbency under pressure after 60 mins represented by the following Mathematical Formula 3, $$\text{AUP}(g/g) = [Wb(g) - Wa(g)]/\text{weight of absorbent polymer}(g) \quad \text{[Mathematical Formula 3]}$$

AUP (g/g)=[Wb(g)−Wa(g)]/weight of absorbent polymer (g)

in Mathematical Formula 3,

Wa (g) is the sum of the weight of the absorbent polymer and the weight of the device capable of providing load to the absorbent polymer, and Wb (g) is the sum of the weight of the absorbent polymer in which moisture is absorbed under load (0.7 psi) for a given time of 10 mins or 60 mins and the weight of the device capable of providing load to the absorbent polymer.

The present invention can provide the synergy effect owing to the complex property combination of the parameter according to the particle size distribution of the SAP represented by Mathematical Formulae 1 and 2 and the absorbency under pressure after a certain time passed. Therefore, the present invention can induce the excellent comfortable wearing sensation by providing the SAP having excellent properties.

At this time, the particle size distribution may be calculated by the parameter known as "SPAN". Therefore, the SPAN can be measured through the particle size distribution of the prepared SAP. In Mathematical Formula 1, D means the particle diameter of the SAP represented by "μm" and it may be measured by a laser particle size analyzer but it is not limited to or by this. Furthermore, when the final SAP particles of 150 to 850 μm are uniformly classified and they are arranged in order of particle diameter, D(10%) means the diameter of the particle when the accumulated weight from the smallest particle becomes 10 weight % based on the total weight of the classified particles. And, D(50%) means the diameter of the particle when the accumulated weight from the smallest particle becomes 50 weight % based on the total weight of the classified particles, when the SAP particles are arranged in order of particle diameter. And, D(90%) means the diameter of the particle when the accumulated weight from the smallest particle becomes 90 weight % based on the total weight of the classified particles, when the SAP particles are arranged in order of particle diameter.

When the SPAN value represented by Mathematical Formula 1 is larger than 1.2, it causes problems of the property deterioration and the dust flying phenomenon because of irregular particle size distribution. And, when the condition of the absorbing rate under load (pressure) (ARUL) represented by Mathematical Formula 2 is less than 0.7, the final sanitary fittings cannot have enough absorbing power and moisture comes out because the absorbing rate under load decreases. At this time, the factors affecting the ARUL value may be the crosslinking density of the crosslinked polymer, the surface treatment density, the uniformity of the particle size of the base polymer, the uniformity of the distribution of the surface treating agent, and so on. Therefore, it is important that the ARUL value accords with the condition of Mathematical Formula 2 in the present invention, and it is preferable for this to use the crosslinked polymer surface-treated by the method disclosed below as the SAP.

And, according to the present invention, it is possible to provide excellent properties to the final SAP by controlling the particle size distribution of the base polymer after preparing and classifying the same.

Namely, when the particle size of the base polymer is distributed from 150 to 850 μm after the classification of the base polymer, it is possible to show the excellent properties that the present invention intends to realize. Specifically, the present invention can improve the particle size and the properties of the SAP when the content of the base polymer of 300 to 600 μm is high. For example, the excellent properties of the present invention can be achieved by classifying the base polymer so that the content of the base polymer of 300 to 600 μm is about 50 weight % or more or about 60 weight % or more, for example, about 50 to 80 weight %, per the total base polymer, and the content of the base polymer 600 to 850 μm and 150 to 300 μm is about 7 weight % or more or about 10 weight % or more, for example, 7 to 20 weight %, per the total base polymer and preparing the SAP by using the base polymer. At this time, the remaining content of the particles below 150 μm and over 850 μm may be less than about 1 weight % or less than about 0.8 weight % per the total base polymer.

Meanwhile, the SAP satisfying above properties may have the water holding property of 25 g/g to 50 g/g, measured according to EDANA method WSP 241.2, and the content of waster-soluble component of 15 weight % or less, measured according to EDANA method WSP 270.2.

Meanwhile, the SAP may include a crosslinked polymer obtained by crosslinking the surface of the powdery base polymer polymerized from at least partially neutralized water-soluble ethylenic unsaturated monomer including an acid group with a $C_2$-$C_8$ diol-based or glycol-based compound.

And, since the crosslinking density of the crosslinked polymer may be the factor affecting the ARUL value, it is preferable to crosslink the surface of the base polymer according to the method of the present invention.

Furthermore, according to another embodiment of the present invention satisfying said properties, a method of preparing the SAP including the steps of preparing a monomer composition including a water-soluble ethylenic unsaturated monomer and a polymerization initiator; preparing a hydrogel polymer by polymerizing said monomer composition in a polymerization reactor; drying and pulverizing said hydrogel polymer; classifying said pulverized hydrogel polymer; and treating the surface of said hydrogel polymer by spraying a surface treatment solution including water and a surface crosslinking agent on each of the classified hydrogel polymer particles is provided.

Namely, since the present invention carries out the proper classification after drying the hydrogel polymer and the treatment of the surface of the classified hydrogel polymer with a specific surface treatment solution and conditions, it is possible to provide a preparation method of the SAP fine particles not only making the control of particle size easy but also providing the SAP having uniform particle size and superior in both of the initial absorbency and the water absorbing power under a long time pressure. The classification process is for providing the base polymer, and thus the classified hydrogel polymer may include the base polymer. Such base polymer may have the average particle size distribution of 150 to 850 μm. And, the excellent properties may be achieved by controlling the distribution ratio of the base polymer of 300 to 600 μm, the base polymer of 600 to 850 μm, and the base polymer of 150 to 300 μm. More concretely, since the present invention prepares the SAP by using the classified base polymer of which the base polymer of 300 to 600 μm is about 50 weight % or more or about 60 weight % or more, for example, about 50 to 80 weight %, per the total base polymer, and the base polymer of 600 to 850 μm and 150 to 300 μm is about 7 weight % or more or about 10 weight % or more, for example, 7 to 20 weight %, per the total base polymer, it is possible to show excellent initial absorbency and to provide a synergy effect of improving the absorbing ratio under non loading condition and the absorbency under pressure conflict with each other at the same time.

The pulverized hydrogel polymer may be a powdery base resin (namely, base polymer) prepared by polymerizing at least partially neutralized water-soluble ethylenic unsaturated monomer including an acid group. At this time, the water-soluble ethylenic unsaturated monomer may include one or more monomers selected from the group consisting of: anionic monomers of acrylic acid, methacrylic acid, maleic anhydride, fumaric acid, crotonic acid, itaconic acid, 2-acryloyl ethane sulfonic acid, 2-methacryloyl ethane sulfonic acid, 2-(meth)acryloyl propane sulfonic acid, and 2-(meth)acrylamide-2-methyl propane sulfonic acid, and salts thereof; nonionic hydrophilic monomers of (meth)acrylamide, N-substituted (meth)acrylate, 2-hydroxyethyl (meth)acrylate, 2-hydroxypropyl(meth)acrylate, methoxy polyethyleneglycol(meth)acrylate, and polyethyleneglycol (meth)acrylate; and amino-containing unsaturated monomers of (N,N)-dimethylaminoethyl (meth)acrylate and (N,N)-dimethylaminopropyl (meth)acrylamide, and a quaternary compound thereof.

And, the present invention can control the crosslinking density of the surface of the classified hydrogel polymer by spraying the specific surface treatment solution on the base resin through the step of treating the surface of the hydrogel polymer. The crosslinking density of the crosslinked polymer prepared by such method may be 0.1 to 1.0 weight % based on the base resin.

The surface treatment solution of the present invention may be an aqueous solution including water as a solvent and a diol-based or glycol-based compound as the surface crosslinking agent, and it may further include a solvent such as other kinds of diols, methanol, and so on with necessity.

The surface crosslinking agent included in the surface treatment solution may be a $C_2$-$C_8$ diol-based or glycol-based compound. Specifically, the diol-based compound may be one or more compound selected from the group consisting of 1,3-propanediol, 2,3,4-trimethyl-1,3-pentanediol, 2-butene-1,4-diol, 1,4-butanediol, 1,3-butanediol, 1,5-pentanediol, 1,6-hexanediol, and 1,2-cyclohexanedimethanol. The glycol compound may be one or more compound selected from the group consisting of monoethyleneglycol, diethyleneglycol, triethyleneglycol, tetraethyleneglycol, polyethyleneglycol, propyleneglycol, dipropyleneglycol, polypropyleneglycol, glycerol, and polyglycerol. More preferably, 1,3-propanediol may be used as the surface crosslinking agent, and propyleneglycol may be used. If 2 or more kinds of the surface crosslinking agent are used in the present invention, the mixing weight ratio of them may be 2:8 to 8:2 based on the weight of the total surface crosslinking agent.

The surface treatment solution may further include an organic solvent. The organic solvent may be one or more compound selected from organic alcohols and diols. At this time, diol compounds can be used as not only the crosslinking agent but also the organic solvent. And glycol ether compounds can be used in addition with necessity.

Preferably, the organic solvent may be one or more compounds selected from the group consisting of ethanol, methanol, isopropylalcohol, ethyleneglycol, propyleneglycol, polyethyleneglycol, ethyleneglycol diglycidyl ether, and polypropyleneglycol.

The concentration of the surface crosslinking agent may be 0.1 to 10 weight %, and preferably 0.3 to 8 weight %, per the total surface treatment solution. At this time, when the concentration of the surface crosslinking agent is below 0.1 weight %, there is a problem of not inducing sufficient reaction, and when it is over 10 weight %, there is a difficulty in the control because of excessive reaction and increased viscosity. Therefore, it is preferable to use the surface crosslinking agent within the range of the present invention.

And, the content of water is not limited particularly because it is used for making the surface treatment solution in the form of aqueous solution, and it may be the remaining content of the total surface treatment solution. And, when the surface treatment solution further includes the organic solvent, it may be 0.1 to 10 weight % based on the total surface treatment solution, and even in this case, the content of water is not limited particularly because the remaining content can be filled with water.

The surface crosslinking agent can be used through a pipe form or a nozzle but it is preferable that the solution is sprayed on the surface of the hydrogel polymer through the nozzle.

At this time, the spraying speed of the surface treatment solution is not limited particularly but it is preferable to control the spray angle and the amount.

The spray angle of the surface treatment solution may be controlled to be 1 to 45°, and preferably 10 to 30°, from the hydraulic nozzle of the spraying device, and it is preferable to spray the surface treatment solution on the substrate on which the classified hydrogel polymer is spread. When the spray angle is blow 1°, there is a problem that the surface treatment solution is intensively sprayed on narrow area and the surface treatment becomes uneven. And when it is over 45°, the solution may be sprayed outside the area on which the hydrogel polymer is spread and it may cause the loss of the surface treatment solution.

And, it is preferable for the surface treatment to spray the surface treatment solution with the amount of 2 to 10 parts by weight, and preferably 3 to 8 parts by weight, per 100 parts by weight of the classified hydrogel polymer.

The device for spraying the surface treatment solution of the present invention may be equipped with means of controlling the spray angle and the spray speed of the treatment solution separately, and may further equipped with a means of controlling temperature with necessity.

Furthermore, the step of treating the surface may include the steps of feeding the classified hydrogel polymer to a surface crosslinking reactor, and carrying out a surface crosslinking reaction of the hydrogel polymer at 120 to 250° C. for 10 to 120 mins. The surface crosslinking reactor may be equipped with a means of controlling temperature. When the crosslinking reaction time is below 10 mins, it is too short to carry out a sufficient crosslinking reaction. And, when the crosslinking reaction time is over 120 mins, the properties of the SAP gets worse in reverse due to excessive surface crosslinking reaction, and the polymer may be decomposed in the reactor due to the long term residue.

According to the present invention, the step of drying and pulverizing the hydrogel polymer may be carried out so that the particle size of the dried hydrogel polymer becomes 150 to 850 μm.

Furthermore, it is preferable to classify the pulverized hydrogel polymer into 2 grades or more according to the particle size in the classifying step. In this case, the classifying step may include the steps of classifying the pulverized hydrogel polymer into 2 grades of the particle size below 150 μm and the particle size of 150 μm to 850 μm; classifying the pulverized hydrogel polymer into 3 grades of the particle size below 150 μm, the particle size of 150 μm or more and below 300 μm, and the particle size of 300 μm to 850 μm; or classifying the pulverized hydrogel polymer into 4 grades of the particle size below 150 μm, the particle size of 150 μm or more and below 300 μm, the particle size of 300 μm or more and below 600 μm, and the particle size of 600 μm to 850 μm. Furthermore, it may further include the step of classifying the particles of 850 μm or more that is included in small quantities in the pulverized hydrogel polymer.

And, in the preparation method according to said embodiments, the steps and methods for preparing the SAP which are commonly being used in the related technical field can be used in the step before the classifying step.

The temperature and the time for drying the hydrogel polymer may be adequately selected according to the moisture content of the prepared hydrogel polymer, and it may be preferable to carry out the drying process at the temperature of 160 to 190° C. for 20 to 40 mins. When the drying temperature is below 160° C., the drying effect is marginal, the drying time grows excessively longer, and it is difficult to make the moisture content be 10 weight % or less. And, when the drying temperature is higher than 190° C., only the surface of the hydrogel polymer is locally and excessively dried and the property of product deteriorates, and the absorptivity under pressure tends to decrease because plenty of fine powders is formed in the succeeding pulverizing step.

The detailed device for drying are not limited particularly, and for example, the drying step may be carried out by infrared ray radiation, hot air, microwave radiation, or UV ray radiation. And, the drying temperature and the time may be adequately selected according to the moisture content of the polymer prepared by the UV polymerization, and it may be preferable to carry out the drying process at the temperature of 80 to 200° C. for 20 to 120 mins. When the drying temperature is below 80° C., there is a problem that the drying effect is marginal and the drying time grows excessively longer, and when the drying temperature is higher than 200° C., there is a problem that the SAP is thermal-degraded.

The pulverization of the dried hydrogel polymer and the surface-treated hydrogel polymer may be carried out according to a common method for pulverizing a resin polymer without limitation. Preferably, any pulverizing machine selected from the group consisting of a pin mill, a hammer mill, a screw mill, a roll mill, and the like may be used in the pulverizing process. At this time, it is preferable that the average diameter of the final SAP particles is 150 to 850 μm after the pulverizing process.

At this time, the moisture content of the hydrogel polymer obtained by the polymerization is generally 30 to 60 weight % but the moisture content after dry of the hydrogel polymer obtained through the drying process may be 1 to 10 weight %. At this time, the moisture content of the hydrogel polymer is the content of moisture in the whole weight of the hydrogel polymer, and it means the value that the weight of the dried polymer is subtracted from the weight of the hydrogel polymer.

The present invention may further include the step of pulverizing and classifying the hydrogel polymer into the particles having the particle size of 150 to 850 μm after the step of treating the surface of the hydrogel polymer.

According to the present invention, the method may further include the step of pulverizing the hydrogel polymer to have the particle size of 1 mm to 15 mm after the polymerization and before the step of drying the hydrogel polymer. At this time, when the particle size of the hydrogel polymer is below 1 mm, it is technically difficult because of the high moisture content of the hydrogel polymer and cohesion of the pulverized particles may occur. And, when the hydrogel polymer is pulverized so that the particle size is over 15 mm, the effect of increasing the efficiency of succeeding drying step according to the pulverization becomes marginal.

Meanwhile, the method of the present invention may prepare the SAP by using a polymerization device equipped with a reactor for preparing a common hydrogel polymer. And the device may be further equipped with the device for classifying the hydrogel polymer into 2 grades or more and the spray device which can control the spray conditions of the surface treatment solution.

The polymerization of the monomer composition may be carried out according to a UV polymerization or a thermal polymerization, and the conditions are not limited particularly and it may be carried out according to common methods. For example, the polymerization may be carried out at the temperature of 25 to 99° C. for 10 secs to 30 mins. Specifically, the thermal polymerization may be classified into a redox polymerization that is carried out at the temperature of 25 to 50° C. for 2 to 30 mins and a thermal polymerization that is carried out at the temperature of 40 to 90° C. for 2 to 30 mins. And, the UV polymerization (photo-polymerization) may be carried out in a wide temperature range of 25 to 99° C. by irradiating with lights for 10 secs to 5 mins because the temperature does not largely influence on the UV polymerization. Furthermore, the intensity of the UV radiation may be 0.1 to 30 mW/cm². The light source and the wavelength range well known to the related art can be used in the UV radiation.

In the method of thermal polymerization or UV polymerization of the monomer composition, the polymerization device used is not limited particularly. For example, the thermal polymerization may be carried out generally in a reactor equipped with a stirring spindle, like a kneader, and the UV polymerization (photo-polymerization) may be carried out in a reactor equipped with a continuously moving conveyor belt. However, said polymerization methods are just examples and the present invention is not limited to or by said polymerization methods.

For example, the hydrogel polymer obtained according to the thermal polymerization that is carried out in the reactor like a kneader equipped with a stirring spindle by providing a hot air thereto or heating the reactor may have the particle size of several centimeters to several millimeters when it is discharged from the outlet of the reactor, according to the shape of the stirring spindle equipped in the reactor. Specifically, the size of the obtained hydrogel polymer may vary according to the concentration and the feeding speed of the monomer composition fed thereto, and generally the hydrogel polymer having the particle size of 2 to 50 mm may be obtained.

And, when the photo-polymerization is carried out by using the reactor equipped with the continuously moving conveyor belt, the hydrogel polymer may be obtained in a sheet form having the width of the belt. At this time, the thickness of the polymer sheet may vary according to the concentration and the feeding speed of the monomer composition fed thereto, and it is preferable to feed the monomer composition so that the polymer sheet having the thickness of 0.5 to 5 cm is obtained. When the monomer composition is fed so that the thickness of the polymer sheet becomes too thin, it is undesirable because of the low production efficiency, and when the thickness of the polymer sheet is over 5 cm, the polymerization reaction may not be occurred evenly through the thickness because of the excessively thick thickness.

The monomer composition may be prepared by mixing the monomer and the polymerization initiator in a mixer equipped with a raw material feeder and a solvent feeder.

And, details of each monomer for the monomer composition are explained.

It is preferable that the polymerization of the water-soluble ethylenic unsaturated monomer is carried out in an aqueous solution in the present invention.

The water-soluble ethylenic unsaturated monomer is not limited if it is a usual monomer for preparing the SAP. For example, one or more monomers selected from the group consisting of an anionic monomer and a salt thereof, a nonionic hydrophilic monomer, and an amino-containing unsaturated monomer and a quaternary compound thereof may be used.

For example, the water-soluble ethylenic unsaturated monomer may be one or more compounds selected from the group consisting of anionic monomers such as acrylic acid, methacrylic acid, maleic anhydride, fumaric acid, crotonic acid, itaconic acid, 2-acryloyl ethane sulfonic acid, 2-methacryloyl ethane sulfonic acid, 2-(meth)acryloyl propane sulfonic acid, and 2-(meth)acrylamide-2-methyl propane sulfonic acid, and salts thereof; nonionic hydrophilic monomers such as (meth)acrylamide, N-substituted (meth)acrylate, 2-hydroxyethyl(meth)acrylate, 2-hydroxypropyl(meth)acrylate, methoxy polyethylene glycol(meth)acrylate, and polyethylene glycol (meth)acrylate; and amino-containing unsaturated monomers such as (N,N)-dimethylaminoethyl (meth)acrylate and (N,N)-dimethylaminopropyl (meth)acrylamide, and a quaternary compound thereof. Preferably, the water-soluble ethylenic unsaturated monomer may be acrylic acid and a salt thereof because they have advantage in the excellent properties.

The concentration of the water-soluble ethylenic unsaturated monomer in the monomer composition may be adequately selected by considering the polymerization time and the reaction conditions, and it may be 35 to 50 weight % preferably. When the concentration of the water-soluble ethylenic unsaturated monomer is below 35 weight %, there are problems of low yield rate and low economic feasibility, and when it is over 50 weight %, it is disadvantageous because the monomer solubility decreases.

The polymerization initiator may be any one compound selected from the group consisting of an azo-based initiator, a peroxide-based initiator, a redox-based initiator, an organic halide initiator, acetophenone, benzoin, benzophenone, benzyl compounds, and a derivative thereof. For example, the polymerization initiator may be acetophenone, benzoin, benzophenone, benzyl compounds, or a derivative thereof, and it may be one or more photo initiators selected from the group consisting of acetophenone derivatives such as diethoxy acetophenone, 2-hydroxy-2-methyl-1-phenylpropane-1-on, benzyl dimethyl tar, 4-(2-hydroxy ethoxy)phenyl-(2-hydroxy)-2-propyl ketone, 1-hydroxycyclohexylphenyl ketone, and so on; benzoin alkyl ethers such as benzoin methyl ether, benzoin ethyl ether, benzoin isopropyl ether, benzoin isobutyl ether; benzophenone derivatives such as methyl o-benzoylbenzoate, 4-phenyl benzophenone, 4-benzoyl-4'-methyl-diphenyl sulfide, (4-benzoyl benzyl)trimethyl ammonium chloride, and so on; thioxanthone-based compounds; acyl phosphine oxide derivatives such as bis(2, 4,6-trimethylbenzoyl)-phenyl phosphine oxide, diphenyl(2, 4,6-trimethylbenzoyl)-phosphine oxide, and so on; and azo-based compounds such as 2-hydroxy methyl propionitrile, 2,2'-[azobis(2-methyl-N-(1,1'-bis(hydroxymethyl)-2-hydroxyethyl)propionamide)].

The polymerization initiator may be used in the amount of 0.01 to 1.0 weight % per the whole monomer composition.

The monomer composition according to the present invention may further include a cross-linking agent.

The cross-linking agent may be one or more compounds selected from the group consisting of cross-linking agents having the water-soluble substituent of the ethylenic unsaturated monomer, at least one functional group which can react with the water-soluble substituent of the ethylenic unsaturated monomer, and at least one ethylenic unsaturated group, and a mixture of them; cross-linking agents having the water-soluble substituent of the ethylenic unsaturated monomer and at least two functional groups which can react with the water-soluble substituent formed by the hydrolysis of a vinyl monomer, and a mixture of them. The cross-linking agent having two or more ethylenic unsaturated groups may be a $C_8$-$C_{12}$ bis acrylamide or bis methacrylamide, a poly (meth)acrylate of $C_2$-$C_{10}$ polyol, a poly(metha)allylether of $C_2$-$C_{10}$ polyol, and the like, and one or more agents selected from the group consisting of N,N'-methylenebis(meth)acrylate, ethyleneoxy(meth)acrylate, polyethyleneoxy(meth) acrylate, propyleneoxy(meth)acrylate, glycerine diacrylate, glycerine triacrylate, trimethylolpropane triacrylate, triallyl amine, triaryl cyanurate, triallyl isocyanate, polyethylene glycol, diethylene glycol, and propylene glycol may be used.

The cross-linking agent may be used in the amount of 0.01 to 1.0 weight % per the whole monomer composition.

Hereinafter, the action and the effect of the present invention are explained in more detail through specific Examples of the invention. However, the following examples are only for illustrating the present invention, and the scope of a right of the invention is not limited to or by them.

EXAMPLE 1

The aqueous monomer solution composition was prepared by mixing 100 g of acrylic acid, 0.5 g of polyethyleneglycol diacrylate (Mw=523) as a crosslinking agent, 0.033 g of diphenyl(2,4,6-trimethylbenzoyl)-phosphine oxide as a UV initiator, 83.3 g of 50% sodium hydroxide (NaOH), and 89.8 g of water. The monomer concentration in the composition was 45 weight %.

And then, after feeding the aqueous monomer solution composition to the continuously moving conveyor belt reactor through the feeder, the hydrogel polymer was prepared by irradiating the composition with UV rays (intensity: 2 mW/cm$^2$) for 2 mins by using a UV radiation device.

After transferring the hydrogel polymer to a cutting machine, it was cut into 0.2 cm. At this time, the moisture content of the cut hydrogel polymer was 50 weight %.

Subsequently, the hydrogel polymer was dried in a hot air dryer of 160° C. for 30 mins, and the dried hydrogel polymer was pulverized by using a pin mill pulverizer. And then, it was classified into the polymer having the particle size (average particle diameter) below 150 μm and the polymer having the particle size of 150 μm to 850 μm by using a sieve.

And then, base polymer BP-1 of SPAN 1.0 was prepared through the particle size control of the classified hydrogel polymer. Furthermore, base polymer BP-2 of SPAN 1.1 was prepared through the particle size control. Finally, base polymer BP-3 of SPAN 1.3 was prepared through the particle size control. At this time, the standard of the classification of each base polymer was as disclosed in Table 1.

Hereafter, the surface of the SAP was treated by spraying 5 parts by weight of the surface treatment solution including 1 weight % of ethyleneglycol diglycidyl ether, 2 weight % of propyleneglycol, and 97 weight % of water on 100 parts by weight of base polymer BP-1. At this time, the surface treatment solution was sprayed on the surface of the hydrogel polymer with the spray angle of 15° through a spraying device. Furthermore, after the classified hydrogel polymer was fed to a surface crosslinking reactor, the surface crosslinking reaction of the hydrogel polymer was carried out at the temperature of 130° C. for 40 mins, in the step of treating the surface.

The hydrogel polymer was pulverized after the surface treatment, and the surface-treated SAP having the average particle diameter of 150 to 850 μm was obtained by using a sieve.

EXAMPLE 2

The SAP was prepared substantially according to the same method as in Example 1, except that the surface treatment solution including 5 weight % of 1,3-propanediol, 5 weight % of propyleneglycol, and 90 weight % of water.

EXAMPLE 3

The SAP was prepared substantially according to the same method as in Example 1, except that base polymer BP-2 was used instead of base polymer BP-1.

EXAMPLE 4

The SAP was prepared substantially according to the same method as in Example 2, except that base polymer BP-2 was used instead of base polymer BP-1.

COMPARATIVE EXAMPLE 1

The SAP was prepared substantially according to the same method as in Example 1, except that base polymer BP-3 was used instead of base polymer BP-1.

COMPARATIVE EXAMPLE 1

The SAP was prepared substantially according to the same method as in Example 2, except that base polymer BP-3 was used instead of base polymer BP-1.

EXPERIMENTAL EXAMPLES

Evaluation on the Moisture Content and the Properties of the SAP

Experimental Example 1

Evaluation on the Moisture Content

The particle size of the base polymers used in Examples and Comparative Examples was measured according to EDANA method WSP 220.2, and the particle size of each base polymer was listed in Table 1.

TABLE 1

|  |  | Base polymer BP-1 | Base polymer BP-2 | Base polymer BP-3 |
|---|---|---|---|---|
| Moisture content (weight %) |  | 1.2 | 1.2 | 1.2 |
| Particle size | 850 μm or more | 0.57 | 0.57 | 0.57 |
|  | 600~850 μm | 15 | 17 | 27 |
|  | 300~600 μm | 68.62 | 61.62 | 41.43 |
|  | 150~300 μm | 15 | 20 | 29 |
|  | 90~150 μm | 0.81 | 0.81 | 2 |
|  | 45~90 μm | 0 | 0 | 0 |
|  | below 45 μm | 0 | 0 | 0 |

From the results of Table 1, the properties of the Examples (BP-1 and BP-2) and the Comparative Examples (BP-3) using the base polymers having different particle size distribution in the range of 90 to 600 μm were relatively evaluated. At this time, the properties of the base polymers were similar except the difference in the particle size.

Namely, the base polymers used in the Examples were classified so that the base polymer of 300 to 600 μm was about 60 weight % or more per the total base polymer and each of the base polymers of 600 to 850 μm and 150 to 300 μm were about 10 weight % or more respectively per the total base polymer.

Experimental Example 2

Evaluation on the Properties

The following tests were carried out in order to evaluate the properties of the SAPs of Examples and Comparative Examples. And, the properties of the absorbent polymers of Examples and Comparative Examples were measured by the following methods and the results are listed in Table 2.

(1) Measurement on the SPAN Value

To the SAPs of Examples and Comparative Examples, the particle size was analyzed according to the particle size analysis method of EDANA method WSP 220.2, and the SPAN value was calculated according to the following equation.

$$\text{SPAN} = [D(90\%) - D(10\%)]/D(50\%) \quad \text{[Mathematical Equation 1-1]}$$

in Mathematical Formula 1-1,

D(90%) is the diameter of the particle when the accumulated weight from the smallest particle becomes 90 weight %, D(10%) is the diameter of the particle when the accumulated weight from the smallest particle becomes 10 weight %, and D(50%) is the diameter of the particle when the accumulated weight from the smallest particle becomes 50 weight %.

(2) Measurement on the Absorbing Rate Under Load (ARUL)

To the SAPs of Examples and Comparative Examples, the ARUL value was measured according to the following Equations.

$$\text{ARUL} = \text{AUP}(10\text{ min})/\text{AUP}(60\text{ min}) \quad \text{[Mathematical Equation 2-1]}$$

in Mathematical Formula 2-1,

ARUL is the absorbing rate under load, AUP (10 min) is the absorbency under pressure after 10 mins represented by the following Mathematical Formula 3, and AUP (60 min) absorbency under pressure after 60 mins represented by the following Mathematical Formula 3, $$\text{AUP}(g/g) = [Wb(g) - Wa(g)]/\text{weight of absorbent polymer}(g) \quad \text{[Mathematical Equation 3]}$$

in Mathematical Formula 3,

Wa (g) is the sum of the weight of the absorbent polymer and the weight of the device capable of providing load to the absorbent polymer, and Wb (g) is the sum of the weight of the absorbent polymer in which moisture is absorbed under load (0.7 psi) for a given time of 10 mins or 60 mins and the weight of the device capable of providing load to the absorbent polymer.

At this time, the absorbency under pressure (AUP) was measured by the following method.

Namely, a 400 mesh stainless steel net was installed in the bottom of the plastic cylinder having the internal diameter of 60 mm. 0.90 g of the SAP was uniformly scattered on the steel net at the room temperature and the humidity of 50%, and a piston which can provide the load of 4.83 kPa (0.7 psi) uniformly was put on the same. At this time, the external diameter of the piston was slightly smaller than 60 mm, there was no gab between the internal wall of the cylinder and the piston, and the jig-jog of the cylinder was not interrupted. The weight Wa (g) of the device was measured.

After putting a glass filter having the diameter of 90 mm and the thickness of 5 mm in a petri dish having the diameter of 150 mm, a saline solution of 0.90 weight % of sodium chloride was poured in the dish until the surface level became equal to the upper surface of the glass filter. A sheet of filter paper having the diameter of 90 mm was put on the same. Said measuring device was put on the filter paper and the solution was absorbed for 1 hr under the load. After 1 hr, the weight Wb (g) was measured after lifting the measuring device up.

(3) Absorption Ratio Under Non Loading Condition (CRC, Centrifuge Retention Capacity)

To the SAPs of Examples and Comparative Examples, the water holding capacity by the CRC was measured according to EDANA method WSP 241.2.

Namely, after inserting W (g) (about 0.2 g) of each polymer obtained in Examples and Comparative Examples uniformly in a nonwoven bag and sealing the same, it was soaked in a 0.9 weight % saline solution at the room temperature. And, after carrying out the same processes as above except not using the SAP, the weight W1 (g) was measured. Water holding capacity was recognized by calculating CRC (g/g) according to the following equation by using the weight obtained above.

$$CRC(g/g)=\{(W2(g)-W1(g))/W(g)\}-1 \quad \text{[Mathematical Equation 4]}$$

in Mathematical Formula 4,

W (g) is the weight of the absorbent polymer;

W1 (g) is the weight of the device without the absorbent polymer after draining with a centrifugal separator at 250 G for 3 min; and W2 (g) is the sum of the weight of the absorbent polymer in which moisture is absorbed for 30 mins in a 0.9 weight % saline solution at the room temperature, and the weight of the device, after draining with a centrifugal separator at 250 G for 3 min.

(4) Water-Soluble Component (Extractable Content)

The water-soluble component (extractable content) was measured according to the same order and method as disclosed in EDANA method WSP 270.2.

TABLE 2

| | SPAN | ARUL | Absorbency under pressure (g/g) | Absorption ratio under non loading condition (g/g) |
|---|---|---|---|---|
| Example 1 | 1.0 | 0.8 | 25.1 | 30.5 |
| Example 2 | 1.0 | 0.76 | 25.0 | 31.2 |
| Example 3 | 1.1 | 0.79 | 24.6 | 30.1 |
| Example 4 | 1.1 | 0.75 | 24.4 | 30.8 |
| Comparative Example 1 | 1.3 | 0.64 | 23.4 | 28.9 |
| Comparative Example 2 | 1.3 | 0.62 | 23.9 | 29.7 |

From the results of Table 2, it is recognizable that the SAPs of Examples 1 to 4 show the properties beyond the equivalent level in comparison with Comparative Examples 1 and 2. Namely, the Examples of the present invention show the superior initial absorbency and the synergy effect of improving the absorbing ratio under non loading condition and the absorbency under pressure conflict with each other at the same time. And it was possible to provide superior properties to existing SAPs because the Examples of the present invention prepared the SAP by using the classified base polymer of which the base polymer of 300 to 600 μm is about 50 weight % or more or about 60 weight % or more, for example, about 50 to 80 weight %, per the total base polymer, and the base polymer of 600 to 850 μm and 150 to 300 μm is about 7 weight % or more or about 10 weight % or more, for example, 7 to 20 weight %, per the total base polymer.

The invention claimed is:

1. A super absorbent polymer (SAP), comprising
a base polymer powder comprising a crosslinked polymer of at least partially neutralized water-soluble ethylenic unsaturated monomer of acrylic acid; and
a surface crosslinking layer formed on the base polymer powder,
wherein the surface crosslinking layer is obtained by crosslinking the surface of the base polymer powder with a $C_2$-$C_8$ diol-based or glycol-based compound, and the surface crosslinking is performed by spraying a surface treatment aqueous solution comprising the $C_2$-$C_8$ diol-based or glycol-based compound on the base polymer powder with the spray angle of 10 to 30° and carrying out the surface crosslinking reaction at 120 to 250° C. for 10 to 120 minutes,
wherein the SAP has the SPAN value of 1.2 or less, represented by the following Mathematical Formula 1, and
satisfies the absorbing rate under load (ARUL) represented by the following Mathematical Formula 2:

$$\text{SPAN}=[D(90\%)-D(10\%)]/D(50\%)\leq 1.2 \quad \text{[Mathematical Formula 1]}$$

in Mathematical Formula 1,

D(90%) is the diameter of the particle when the accumulated weight from the smallest particle becomes 90%, when the SAP particles are arranged in order of particle diameter measured according to EDANA method WSP 220.2, D(10%) is the diameter of the particle when the accumulated weight from the smallest particle becomes 10%, when the SAP particles are arranged in order of particle diameter measured according to EDANA method WSP 220.2, and D(50%) is the diameter of the particle when the accumulated weight from the smallest particle becomes 50%, when the SAP particles are arranged in order of particle diameter measured according to EDANA method WSP 220.2, $$1.0>\text{ARUL}=\text{AUP}(10\text{ min})/\text{AUP}(60\text{ min})>0.70 \quad \text{[Mathematical Formula 2]}$$

in Mathematical Formula 2,

AUP (10min) is the absorbency under pressure after 10 mins represented by the following Mathematical Formula 3, and AUP (60 min) is the absorbency under pressure after 60 mins represented by the following Mathematical Formula 3, $$\text{AUP}(g/g)=[Wb(g)-Wa(g)]/\text{weight of absorbent polymer}(g) \quad \text{[Mathematical Formula 3]}$$

in Mathematical Formula 3,

Wa (g) is the sum of the weight of the absorbent polymer and the weight of the device capable of providing load to the absorbent polymer, and Wb (g) is the sum of the weight of the absorbent polymer in which moisture is absorbed under load (0.7 psi) for a given time of 10 mins or 60 mins and the weight of the device capable of providing load to the absorbent polymer.

2. The super absorbent polymer according to claim 1, the base polymer powder comprises:
the powder having the diameter of 300 to 600 μm in an amount of 50 weight % or more.

3. The super absorbent polymer according to claim 2, the base polymer powder comprises:
the powder having the diameter of 600 to 850 μm in an amount of 7 weight % or more; and
the powder having the diameter of 150 to 300 μm in an amount of 7 weight % or more.

4. A sanitary fitting including the super absorbent polymer of claim 1.

5. A diaper including the super absorbent polymer of claim 1.

6. A product including the super absorbent polymer of claim 1, wherein the product is a water combination soil for horticulture, a water-stop material for civil engineering and construction, a nursery sheet, a freshness preservation in a food distribution field or a poultice material.

* * * * *